United States Patent
Zreda et al.

(10) Patent No.: US 10,564,112 B2
(45) Date of Patent: Feb. 18, 2020

(54) MODERATED NEUTRON SENSOR

(71) Applicant: QUAESTA INSTRUMENTS, LLC, Tucson, AZ (US)

(72) Inventors: Marek Zreda, Tucson, AZ (US); Steven Hamann, Tucson, AZ (US)

(73) Assignee: QUAESTA INSTRUMENTS, LLC, Tucson, AZ (US)

( * ) Notice: Subject to any disclaimer, the term of this patent is extended or adjusted under 35 U.S.C. 154(b) by 0 days.

(21) Appl. No.: 16/213,812

(22) Filed: Dec. 7, 2018

(65) Prior Publication Data

US 2019/0179041 A1    Jun. 13, 2019

Related U.S. Application Data

(60) Provisional application No. 62/596,315, filed on Dec. 8, 2017.

(51) Int. Cl.
| | |
|---|---|
| *G01N 23/00* | (2006.01) |
| *G01N 33/24* | (2006.01) |
| *G01T 3/00* | (2006.01) |
| *G01T 7/00* | (2006.01) |

(52) U.S. Cl.
CPC ......... *G01N 23/005* (2013.01); *G01N 33/246* (2013.01); *G01T 3/00* (2013.01); *G01T 7/00* (2013.01); *G01T 7/005* (2013.01)

(58) Field of Classification Search
CPC .................................. G01T 3/00; G01T 7/00
See application file for complete search history.

(56) References Cited

U.S. PATENT DOCUMENTS

| | | | |
|---|---|---|---|
| 2,928,965 A | 10/1954 | Bayard et al. | |
| 4,047,042 A | 9/1977 | Wada et al. | 250/390 |
| 4,463,264 A | 7/1984 | Young et al. | 250/390 |
| 4,992,667 A | 2/1991 | Abelentsev et al. | 250/390.05 |
| 5,083,029 A | 1/1992 | Buchanan | 250/390.05 |
| 5,321,269 A * | 6/1994 | Kitaguchi | G01T 3/08 250/252.1 |
| 5,502,303 A | 3/1996 | Gonzalez-Lepera | 250/252.1 |
| 7,078,705 B1 | 7/2006 | Ianakiev et al. | 250/390.01 |
| 7,233,007 B2 | 6/2007 | Downing et al. | 250/390.11 |
| 7,514,694 B2 | 4/2009 | Stephan et al. | 250/390.01 |

(Continued)

OTHER PUBLICATIONS

"Insights into the footprint of the cosmic-ray probe from new field measurements and neutron modeling," COSMOS 5 Workshop, Copenhagen, Aug. 22-24, 2016 (63 pgs).

(Continued)

*Primary Examiner* — Christine S. Kim
(74) *Attorney, Agent, or Firm* — Hayes Soloway P.C.

(57) ABSTRACT

A moderated neutron detector includes a neutron detector having a first volume. A moderating enclosure is positioned around the neutron detector and encloses a second volume. The second volume is between 2 and 80 times larger than the first volume. A method for increased neutron detection includes the following steps: positioning a neutron detector within a moderating enclosure, wherein the neutron detector has a first volume, wherein the moderating enclosure encloses a second volume, and wherein the second volume is between 2 and 80 times larger than the first volume; increasing a quantity of neutrons impingent upon the neutron detector; and measuring the quantity of neutrons impinging upon the neutron detector.

16 Claims, 8 Drawing Sheets

(56) References Cited

U.S. PATENT DOCUMENTS

| | | | |
|---|---|---|---|
| 8,217,360 B2 | 7/2012 | Nukatsuka et al. | 250/370.11 |
| 8,653,470 B2 | 2/2014 | Dubeau | 250/390.07 |
| 8,796,634 B2 | 8/2014 | Kisner et al. | G01T 3/008 |
| 9,029,788 B2 | 5/2015 | Yang et al. | G01T 3/06 |
| 9,081,100 B1* | 7/2015 | Bellinger | G01T 3/085 |
| 9,329,303 B2 | 5/2016 | Inanc et al. | G01V 5/107 |
| 9,395,454 B2 | 7/2016 | Orava et al. | G01T 3/06 |
| 9,442,202 B2 | 9/2016 | Tanner et al. | G01T 3/00 |
| 9,678,229 B2 | 6/2017 | Neyland | G01T 3/008 |
| 9,778,392 B2 | 10/2017 | Justus et al. | G01V 5/0091 |
| 9,817,138 B2 | 11/2017 | McGregor et al. | G01T 3/008 |
| 9,910,170 B1* | 3/2018 | Billiard | G01T 3/02 |
| 9,939,538 B2 | 4/2018 | Ing et al. | G01T 3/06 |
| 9,958,561 B2 | 5/2018 | Bellinger et al. | G01T 3/065 |
| 9,978,384 B2* | 5/2018 | Li | G06F 3/162 |
| 10,024,986 B2 | 7/2018 | Lennert et al. | G01T 3/008 |
| 2001/0046274 A1 | 11/2001 | Craig et al. | 376/154 |
| 2003/0012324 A1 | 1/2003 | Haruyama | 376/159 |
| 2004/0061047 A1 | 4/2004 | Bolozdynya et al. | 250/251 |
| 2006/0023828 A1 | 2/2006 | McGregor et al. | 376/158 |
| 2006/0138340 A1 | 6/2006 | Ianakiev et al. | 250/390.01 |
| 2008/0210880 A1* | 9/2008 | Baroni | G01N 23/2073 250/390.11 |
| 2011/0180718 A1* | 7/2011 | Luszik-Bhadra | G01T 3/00 250/390.03 |
| 2014/0158893 A1 | 6/2014 | Platt et al. | G01T 3/085 |
| 2014/0158895 A1* | 6/2014 | Wang | G01T 3/008 250/375 |
| 2014/0361187 A1 | 12/2014 | Zhao et al. | G01T 3/06 |
| 2015/0241577 A1 | 8/2015 | Spillane et al. | G01T 3/00 |
| 2015/0355345 A1 | 12/2015 | Neyland | G01T 3/008 |
| 2016/0356901 A1 | 12/2016 | Shao et al. | G01T 3/08 |
| 2017/0023684 A1 | 1/2017 | Inglis et al. | G01T 3/008 |
| 2017/0059723 A1 | 3/2017 | Ing et al. | G01T 3/065 |
| 2017/0090049 A1 | 3/2017 | Ramsden et al. | G01T 3/06 |
| 2017/0184736 A1* | 6/2017 | Ramsden | G01T 3/06 |
| 2018/0299570 A1 | 10/2018 | Degtiarenko | G01T 7/00 |

OTHER PUBLICATIONS

Desilets, D., and M. Zreda, 2013. Footprint diameter for a cosmic-ray soil moisture probe: Theory and Monte Carlo simulations. Water Resources Research 49, 3566-3575, doi: 10.1002/wrcr.20187 (10 pgs).

Knoll, G.F., 2000, Radiation detection and measurement: New York, Wiley, 802 p. (81 pgs).

Köhli, M., M. Schrön, M. Zreda, U. Schmidt, P. Dietrich, and S. Zacharias, 2015. Footprint characteristics revised for field-scale soil moisture monitoring with cosmic-ray neutrons. Water Resources Research 51, 5772-5790 (20 pgs).

Lab C Website, www.lab-c.co (7 pgs).

Schrön, M., M. Köhli, L. Scheiffele, J. Iwema, H.R. Bogena, L. Lv, E. Martini, G. Baroni, R. Rosolem, J. Weimar, J. Mai, M. Cuntz, C. Rebmann, S.E. Oswald, P. Dietrich, U. Schmidt, and S. Zacharias, 2017b. Improving calibration and validation of cosmic-ray neutron sensors in the light of spatial sensitivity. Hydrology and Earth System Sciences 21, 5009-5030 (22 pgs).

Schrön, M., Zacharias, S., Womack, G., Köhli, M., Desilets, D., Oswald, S. E., Bumberger, J., Mollenhauer, H., Kögler, S., Remmler, P., Kasner, M., Denk, A., and Dietrich, P., 2017a. Intercomparison of Cosmic-Ray Neutron Sensors and Water Balance Monitoring in an Urban Environment, Geoscientific Instruments, Methods and Data Systems Discussions, https://doi.org/10.5194/gi-2017-34, in review (18 pgs).

Zreda, M., D. Desilets, T.P.A. Ferré, and R.L. Scott, 2008. Measuring soil moisture content non-invasively at intermediate spatial scale using cosmic-ray neutrons. Geophysical Research Letters 35, L21402, doi:10.1029/2008GL035655 (5 pgs).

Zreda, M., W.J. Shuttleworth, X. Zeng, C. Zweck, D. Desilets, T. Franz, and R. Rosolem, 2012. COSMOS: the COsmic-ray Soil Moisture Observing System. Hydrology and Earth System Sciences 16, 4079-4099 (23 pgs).

International Search Report and Written Opinion issued in PCT/US2018/064548 dated Feb. 19. 2019, 11 pgs.

International Search Report and Written Opinion issued in PCT/US2018/064573 dated Feb. 14, 2019, 9 pgs.

Office Action issued in U.S. Appl. No. 16/213,741 dated Feb. 8, 2019, 9 pgs.

Office Action issued in U.S. Appl. No. 16/213,741 dated Mar. 7, 2019, 18 pgs.

Heidbüchel et al., "Use of cosmic-ray neutron sensors for soil moisture monitoring in forests" Hydrol. Earth Syst. Sci., 20, 1269-1288, 2016.

U.S. Appl. No. 16/213,741, filed Dec. 7, 2018, Zreda.

Office Action issued in U.S. Appl. No. 16/213,741 dated Jul. 9, 2019, 22 pgs.

\* cited by examiner

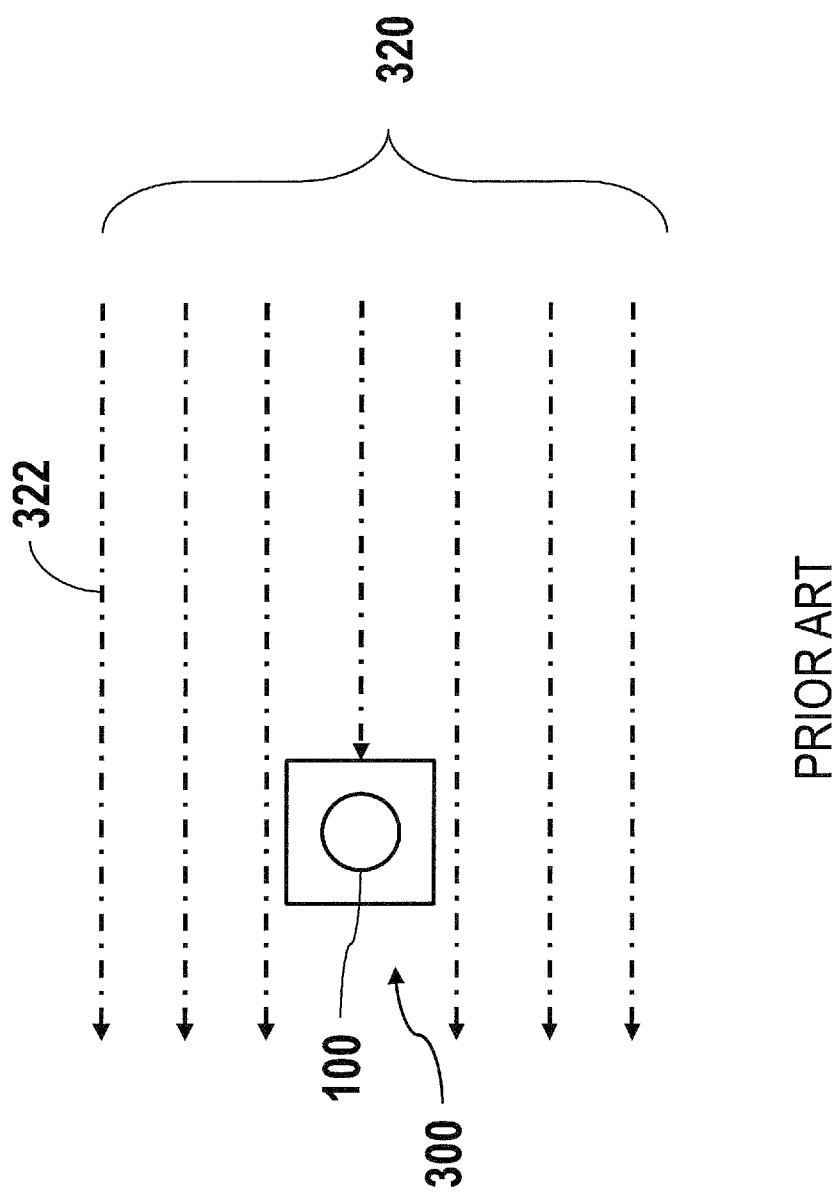

MODERATED NEUTRON SENSOR

CROSS REFERENCE TO RELATED APPLICATION

This application claims benefit of U.S. Provisional Application Ser. No. 62/596,315, titled "Distance and Direction Sensitive Cosmogenic-Neutron Soil Moisture Sensors (CNS)," filed Dec. 8, 2017, the entire disclosure of which is incorporated herein by reference.

FIELD OF THE DISCLOSURE

The present disclosure is generally related to detecting neutrons and more particularly is related to detecting neutrons using an enhanced moderator.

BACKGROUND OF THE DISCLOSURE

Neutron detectors measure epithermal, fast, or high-energy neutrons in a region of neutron flux. These neutrons may originate from a number of sources, including cosmogenic radiation, nuclear fission radiation, and radioactive decay. The mean free path of neutrons in air is long, about 150 meters. When neutrons propagate through air, they tend to travel in straight lines along this distance. However, in a moderating material such as high density polyethylene (HDPE), the neutrons' mean free path is considerably shorter, about 1 millimeter. Neutrons propagating through a moderating material may drastically change their direction of travel in very short distances.

Moderated neutron detectors are known in the art. Most commonly, thermal neutron detectors are surrounded by a moderating material having a high hydrogen content, such as water, paraffin, HDPE, or ultra-high molecular weight plastic (UHMW). The hydrogen in the moderating material causes neutrons having a broad range of energies to elastically scatter from interactions with hydrogen nuclei, losing kinetic energy in the process. The scattering process is highly efficient, and it may rapidly slow fast or epithermal neutrons such that they are slow enough to be measured by a thermal neutron detector. Moderator thicknesses are commonly in the range of about 0.5 inches to about 1.5 inches.

Typical moderator design dictates that the moderator just surrounds the neutron detector, giving the moderator roughly the same size and shape as the detector. This allows the moderator to be small and light. Moderator weight and size can be a concern for certain applications, as moderating material is typically dense compared to the other aspects of the neutron detector. In some applications, the size and weight of the moderator may be constrained by necessity. For example, a moderated neutron detector in a portal monitor may be constrained in size by government regulations. As another example, the weight of a neutron detector deployed on an unmanned aerial vehicle (UAV) may be payload limited based on the aircraft's range and capabilities.

To increase the sensitivity of a neutron detector without a subsequent increase in size or weight, it is common to employ a neutron detector with a higher inherent sensitivity. At a fixed size, the sensitivity of a detector can be increased based on the amount or type of active material utilized in the detector. For example, high pressure Helium-3 (He3) detectors are more sensitive than low pressure He3 detectors. He3 detectors are more sensitive than boron trifluoride (BF3) gas detectors. The four most common neutron proportional counters are He3, BF3, lithium-6 (Li-6) foil, and boron-10 (B10) powder. While He3 is the most sensitive detection material, it may cost as much as five times the other common proportional counter materials. Therefore, it can be costly to increase a neutron detector's sensitivity by using highly sensitive detection material.

Neutron detector sensitivity can also be increased by building a larger detector. For example, the volume or number of detection elements may be increased in order to ensure that the neutron detector interacts with more neutrons in the region of neutron flux. This volume or number increase naturally results in higher cost and higher weight, as the detector material used is increased. Additionally, this increase results in an increase in moderating material, which results in a larger increase in the weight of the neutron detector. As a result, building a larger detector may be unfeasible or impractical for many applications.

Thus, a heretofore unaddressed need exists in the industry to address the aforementioned deficiencies and inadequacies.

SUMMARY OF THE DISCLOSURE

Embodiments of the present disclosure provide an apparatus for detecting neutrons. Briefly described, in architecture, one embodiment of the apparatus, among others, can be implemented as follows. A moderated neutron sensor includes a neutron detector having a first volume. A moderating enclosure is positioned around the neutron detector and encloses a second volume. The second volume is between 2 and 80 times larger than the first volume.

Embodiments of the present disclosure can also be viewed as providing an apparatus for detecting neutrons. Briefly described, in architecture, one embodiment of the apparatus, among others, can be implemented as follows. A moderated neutron sensor includes a neutron detector having an exterior surface. A moderating enclosure is positioned around the neutron detector. The moderating enclosure has an interior surface positioned a spaced distance away from the exterior surface of the neutron detector by at least one half inch.

The present disclosure can also be viewed as providing methods for increased neutron detection. In this regard, one embodiment of such a method, among others, can be broadly summarized by the following steps: positioning a neutron detector within a moderating enclosure, wherein the neutron detector has a first volume, wherein the moderating enclosure encloses a second volume, and wherein the second volume is between 2 and 80 times larger than the first volume; increasing a quantity of neutrons impingent upon the neutron detector; and measuring the quantity of neutrons impinging upon the neutron detector.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3 is a top-view illustration of the neutron detector of FIG. 1A within a field of neutron flux.

DETAILED DESCRIPTION

Figure 1B:
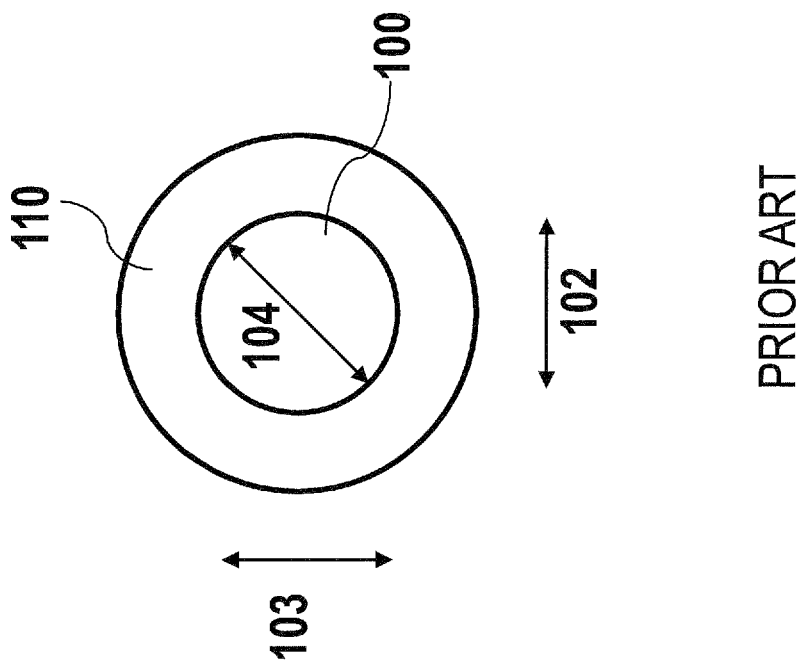
FIG. 1B is a cross-sectional illustration of the neutron detector of FIG. 1A with a moderator.
Figure 1A:
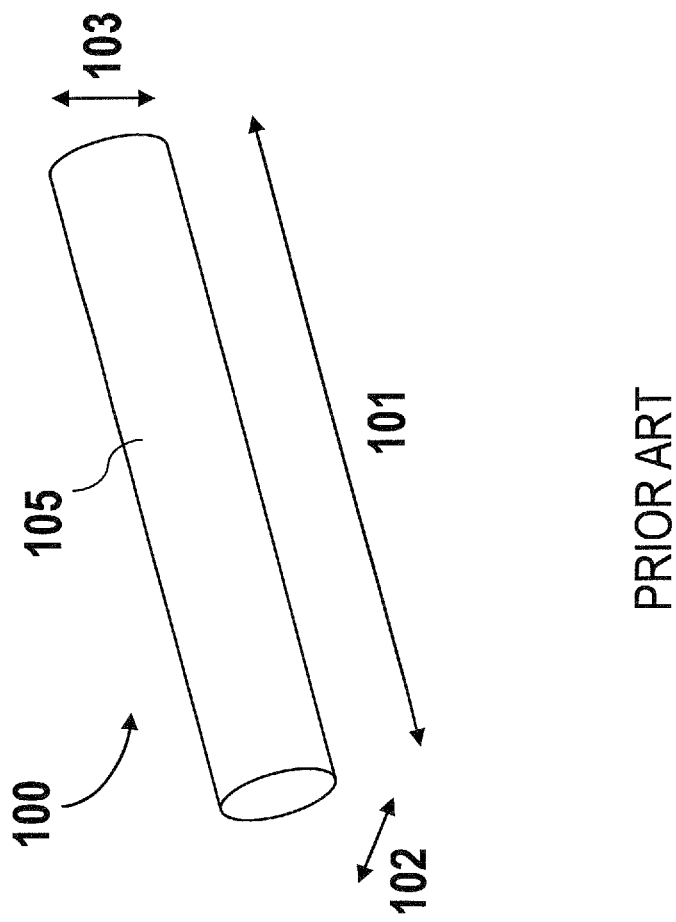
FIG. 1A is an illustration of a neutron detector in a tube form factor.

FIG. 1A is an illustration of a neutron detector 100 in a tube form factor. Tube-shaped neutron detectors 100 ("tube neutron detectors") are known in the art. Tube neutron detectors 100 generally have a volume defined by the detector's length 101, width 102, and depth 103. The length 101, width 102, and depth 103 may be measured along orthogonal axes in three-dimensional space. The length 101 may always be measured down the length of the tube neutron detector 100 without regard to the detector's actual orientation in space. Likewise, the width 102 and depth 103 may always be measured orthogonally across the end face of the tube neutron detector 100 without regard to the detector's actual orientation in space. For example, the tube neutron detector 100 may be oriented vertically during use, such that the length 101 is measured vertically, and the width 102 and depth 103 are measured horizontally. A tube neutron detector 100 may have an exterior surface 105 running the entirety of the tube neutron detector 100. Tube neutron detectors 100 may include any suitable type of neutron detector, including thermal or epithermal neutron detectors such as gas tube proportional counters, scintillators, or solid state detectors.

FIG. 1B is a cross-sectional illustration of the neutron detector 100 of FIG. 1A with a moderator 110. The cross-sectional illustration shows the tube neutron detector 100 having a width 102, depth 103, and diameter 104. A moderator 110 is placed in close fit with the tube neutron detector 100. In one example, the moderator 110 may surround the tube neutron detector 100 at the exterior surface 105 down the length 101 of the tube neutron detector 100. The moderator 110 may have a thickness of about 1 inch, and the volume enclosed by the moderator may be substantially the same volume as the tube neutron detector 100. The volume enclosed by the close fit moderator 110 is a function of the diameter 104 of the detector and the length 101 of the detector as shown in FIG. 1A.

Figure 2B:
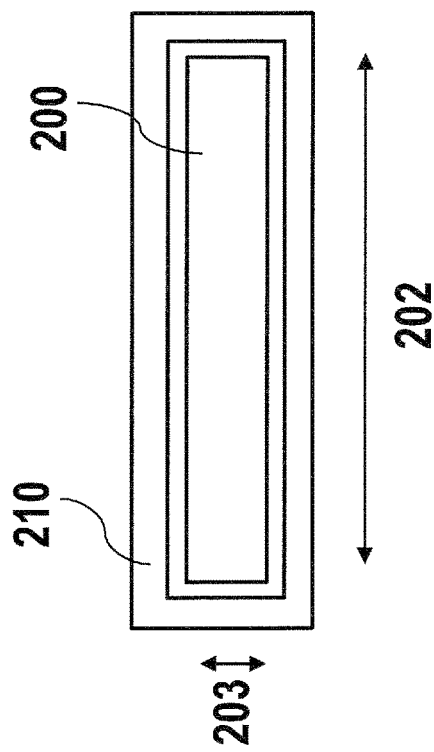
FIG. 2B is a cross-sectional illustration of the neutron detector of FIG. 2A with a moderator.
Figure 2A:
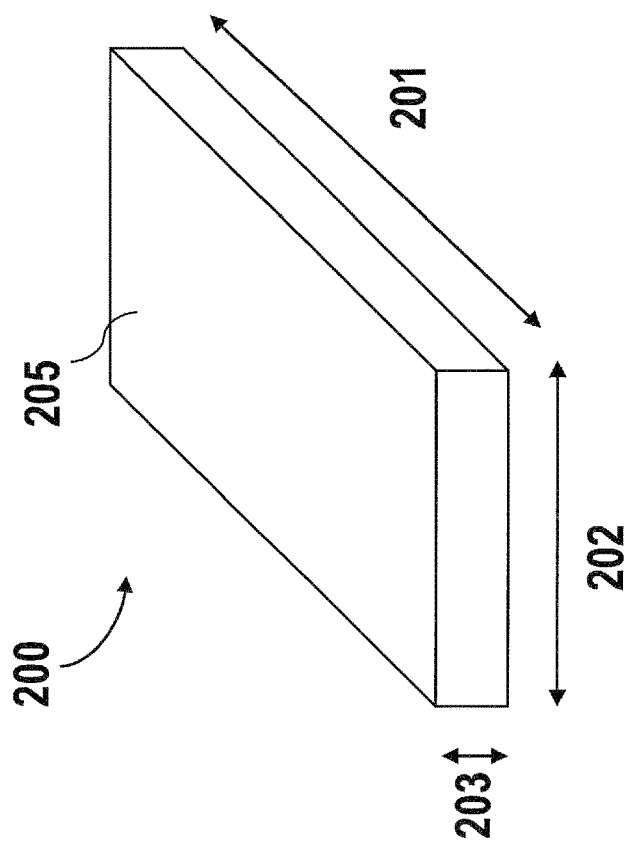
FIG. 2A is an illustration of a neutron detector in a sheet form factor.

FIG. 2A is an illustration of a neutron detector 200 in a sheet form factor ("sheet neutron detector"). Sheet neutron detectors 200 are known in the art. Sheet neutron detectors 200 generally have a volume defined by the detector's length 201, width 202, and depth 203. The length 201, width 202, and depth 203 may be measured along orthogonal axes in three-dimensional space. The length 201 may always be measured down the length of the sheet neutron detector 200 without regard to the detector's actual orientation in space. Likewise, the width 202 and depth 203 may always be measured orthogonally across the end face of the sheet neutron detector 200 without regard to the detector's actual orientation in space. For example, the sheet neutron detector 200 may be oriented horizontally during use, such that the length 201 is measured horizontally, and the width 202 and depth 203 are measured vertically. A sheet neutron detector 200 may have an exterior surface 205 running the entirety of the sheet neutron detector 200. Sheet neutron detectors 200 may include any suitable type of neutron detector, including Li-6 and B10 gas proportional counters, neutron scintillation detectors, and solid state detectors.

FIG. 2B is a cross-sectional illustration of the neutron detector 200 of FIG. 2A with a moderator 210. The cross-sectional illustration shows the sheet neutron detector 200 having a width 202 and depth 203. A moderator 210 is placed in close fit with the sheet neutron detector 200. In one example, the moderator 210 may surround every face of the sheet neutron detector 200 at the exterior surface 205 down the length 201 of the sheet neutron detector 200. The moderator 210 may have a thickness of about 1 inch, and the volume enclosed by the moderator may be substantially the same volume as the sheet neutron detector 200.

The neutron detectors shown in FIGS. 1A-2B are exemplary only. The present disclosure is not limited to any particular shape, form factor, or embodiment of neutron detector, and may be utilized with any suitable neutron detector.

FIG. 3 is a top-view illustration of the neutron detector 100 of FIG. 1A within a field of neutron flux 320. In the example shown in FIG. 3, a tube neutron detector 100 is oriented vertically so that the length of the tube is not visible in the illustration. The tube neutron detector 100 may be surrounded by a close fit moderator, creating a moderated neutron detector known in the prior art ("prior art detector") 300. Neutrons 322 within a field of neutron flux 320 may propagate in relatively straight lines for distances of about 150 meters. Neutrons 322 that propagate in a direction outside of the path of the prior art detector 300 may not impinge upon the tube neutron detector 100 and thus, may not be counted. As shown in FIG. 3, only a very small portion of neutrons 322 within the field of neutron flux 320 may reach the detector 100.

Figure 4:
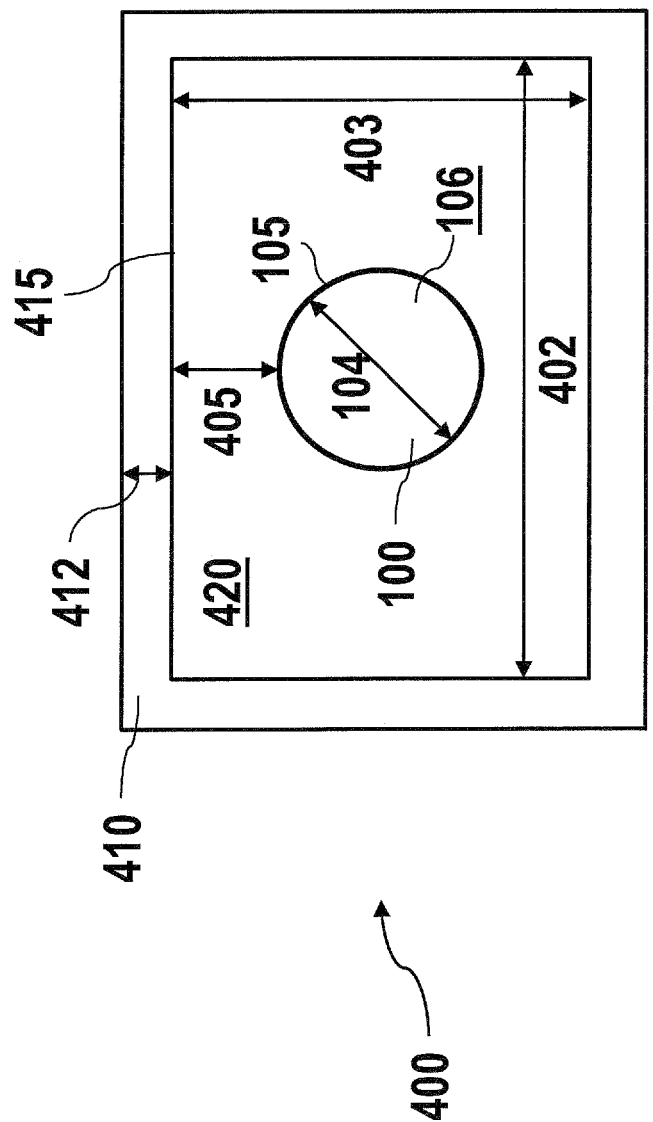
FIG. 4 is a cross-sectional illustration of a tube form factor moderated neutron sensor, in accordance with a first exemplary embodiment of the present disclosure.

FIG. 4 is a cross-sectional illustration of a tube form factor moderated neutron sensor ("moderated neutron sensor") 400, in accordance with a first exemplary embodiment of the present disclosure. The moderated neutron sensor 400 may include a neutron detector 100 having a first volume. A moderating enclosure 410 is positioned around the neutron detector 100 and encloses a second volume. The second volume is between 2 and 80 times larger than the first volume.

The neutron detector ("neutron detector") 100 may be any type, shape, or form of neutron detector suitable for detecting thermal and epithermal neutrons. Detectors of this type may include gas-proportional detectors, scintillation neutron detectors, semiconductor neutron detectors, and the like. The neutron detector 100 may be sized and shaped to detect neutrons over a desired area, within size or weight constraints, or with a desired sensitivity. FIG. 4 shows a cross-section of a tube form factor neutron detector 100. The volume of the neutron detector 100 may be calculated as discussed relative to FIGS. 1A-1B, above, using the diameter 104 and length of the neutron detector. The volume of the neutron detector 100 may be called a first volume.

A moderating enclosure 410 may be positioned around the neutron detector 100. The moderating enclosure 410 may be made from a moderating material capable of interacting with neutrons of a desired energy range. In the example of a hydrogen-sensitive neutron detector 100, the moderating enclosure 410 may be made from a moderating material having a high hydrogen content, such as water, paraffin, HDPE, ultra-high molecular weight plastic (UHMW), or any combination thereof. The moderating enclosure 410 may surround and enclose the entire neutron detector 100. In one example, the thickness 412 of the moderating enclosure 410 may be between 0.5 inches and 2.0 inches. In another example, the thickness 412 of the moderating enclosure 410 may be greater than 2.0 inches. For example, in applications with higher energy, more monoenergetic neutrons, such as a 5 MeV neutron source, the thickness 412 of the moderating enclosure 410 may be about 2.5 inches. The moderating enclosure 410 may enclose a volume, called the second volume. The second volume may be determined from the interior width 402, interior depth 403, and interior length of the moderating enclosure (not shown due to perspective). The interior width 402, interior depth 403, and interior length may be the distance between opposing interior surfaces 415 of the moderating enclosure 410.

The second volume enclosed by the moderating enclosure 410 may be between 2 and 80 times larger than the first volume occupied by the neutron detector 100. In particular, the second volume may be between 2 and 20 times larger than the first volume. More particularly, the second volume may be between 5 and 10 times larger than the first volume. In one example, the ratio of the second volume to the first volume may correlate with an increase in the sensitivity of the moderated neutron sensor 400 up to a maximum value. Thereafter, the second volume enclosed by the moderating enclosure 410 may be too large relative to the first volume of the neutron detector 100 to effectively direct neutrons to the neutron detector 100. The neutrons may actually be directed away from the neutron detector 100 due to the geometry of the moderating enclosure 410 at volume ratios larger than 80 times larger.

In one example, the second volume may be larger than the first volume due primarily to a difference between the depth 103 of the neutron detector 100 (shown in FIG. 1A) and the depth 403 of the moderating enclosure 410. Thus, the difference between the depth 103 of the neutron detector 100 and the interior depth 403 of the moderating enclosure 410 may be larger than the difference between the length 101 of the neutron detector 100 and the length of the moderating enclosure 410. In other words, the moderating enclosure 410 may be spaced a greater distance from the neutron detector 100 along the depth direction than along the length direction. The depth direction may have a more pronounced effect on the moderated neutron sensor 400's sensitivity than the length direction. Thus, a moderated neutron sensor 400 with a deeper moderating enclosure 410 may be more sensitive to neutrons than a moderated neutron sensor 400 with a longer moderating enclosure 410. This effect may depend on the shapes of the neutron detector 100 and the moderating enclosure 410. For instance, a tube-shaped neutron detector 100 may detect more neutrons with a deeper or wider moderating enclosure 410, assuming the neutron detector 100 is located centrally within the moderating enclosure 410. A sheet-shaped neutron detector 200 (shown in FIG. 2A) may detect more neutrons with a deeper moderating enclosure 410.

In one example, the neutron detector 100 may be located centrally within the moderating enclosure 410, meaning that the neutron detector 100 is located substantially at and along the center of the interior 420 of the moderating enclosure 410. This may be particularly true when the moderated neutron sensor 400 includes a single neutron detector 100. When the moderated neutron sensor 400 includes two or more neutron detectors 100, the neutron detectors 100 may not be located centrally.

The moderated neutron sensor 400 may measure neutrons in the 1 eV to 2 MeV range, including all neutrons between epithermal and fast neutrons. Thus, the moderated neutron sensor 400 may be considered a fast or epithermal neutron sensor. By way of example, the moderated neutron sensors shown in this disclosure may be hydrogen-sensitive neutron sensors, although the disclosure is not so limited. Hydrogen-sensitive neutron sensors may detect neutrons having an energy range of 0-2 MeV, which may include cosmogenic neutrons useful for cosmogenic neutron-based soil moisture measurement. The moderating enclosure 410 may generally have a thickness between 0.5 and 2.0 inches, which may allow the hydrogen-sensitive neutron sensor to measure neutrons in the range from 0-2 MeV, and particularly in the range of 1 eV-2 MeV. Other types of neutron sensors may be used for environmental neutron monitoring, radioactive waste monitoring, area or perimeter monitoring around nuclear power plants or uranium mines, portal monitoring, and the like. For example, a sensor for measuring fast neutrons propagating from nuclear waste may have a moderating enclosure 410 thick enough to thermalize neutrons in the energy band around 5 MeV. The thickness 412 of the moderating enclosure 410 may be appropriate for its intended application in conjunction with the neutron detector 100. In one example, the relationship between the neutron detector 100 and the moderating enclosure 410 may be understood as a function of the distance 405 between an exterior surface 105 of the neutron detector 100 and an interior surface 415 of the moderating enclosure 410 ("spaced distance" 405). A moderated neutron detector 400 includes a neutron detector 100 having an exterior surface 105. A moderating enclosure 410 is positioned around the neutron detector 100. The moderating enclosure 410 has an interior surface 415 positioned a spaced distance 405 away from the exterior surface 105 of the neutron detector 100 by at least one half inch. Thus, for any given thickness 412 of the moderating enclosure 410, the moderating enclosure 410 and the neutron detector 100 may be positioned a spaced distance apart. In one example, the spaced distance 405 may be at least 0.5 inches. In another example, the spaced distance may be at least 2 inches. In another example the spaced distance may be at least 3 inches. When the neutron detector 100 and moderating enclosure 400 have different shapes, as shown in FIG. 4, the spaced distance 405 may not be constant at every point between the exterior surface 105 of the neutron detector 100 and the interior surface of the moderating enclosure 100. The spaced distance 405 may be considered to be the minimum distance between any two points on the exterior surface 105 and interior surface 415. In this case, the minimum distance between any two points on the exterior surface 105 and the interior surface 415 may be at least 0.5 inches. In another example, the spaced distance 405 may be measured along the length 101 of the neutron detector 100, but not from an end surface 106 of the neutron detector 100. For instance, when the neutron detector 100 is a tube shape, the ends at either extreme of the tube may form an end surface 106, depicted in FIG. 4 as a circle. In one example, the spaced distance 405 may not be measured from the plane of the end surface 106, but may only be considered from the exterior surface 105 in an orthogonal plane.

The interior 420 between the neutron detector 100 and the moderating enclosure 410 may include anything that is substantially transparent to the passage of neutrons. In one example, the interior 420 may be a vacuum. In another, the interior 420 may be filled with air or another substantially transparent gas. In another example, the interior 420 may be filled with a substantially transparent liquid or solid. Substantially transparent solids may support the neutron detector 100, holding it in place within the moderating enclosure 410.

The moderated neutron sensor 400 may include additional electronic components, such as a power source, communications interface, control hardware, and the like. For portable detectors 400, the power source may be a battery or solar power. The communications interface may allow a user to collect and retrieve neutron data from the moderated neutron detector 400. The communications interface may include communications hardware, such as data ports, antennas, and the like, and may be accessed by wired or wireless communication. The control hardware may allow a user to operate and troubleshoot the device.

Figure 5:
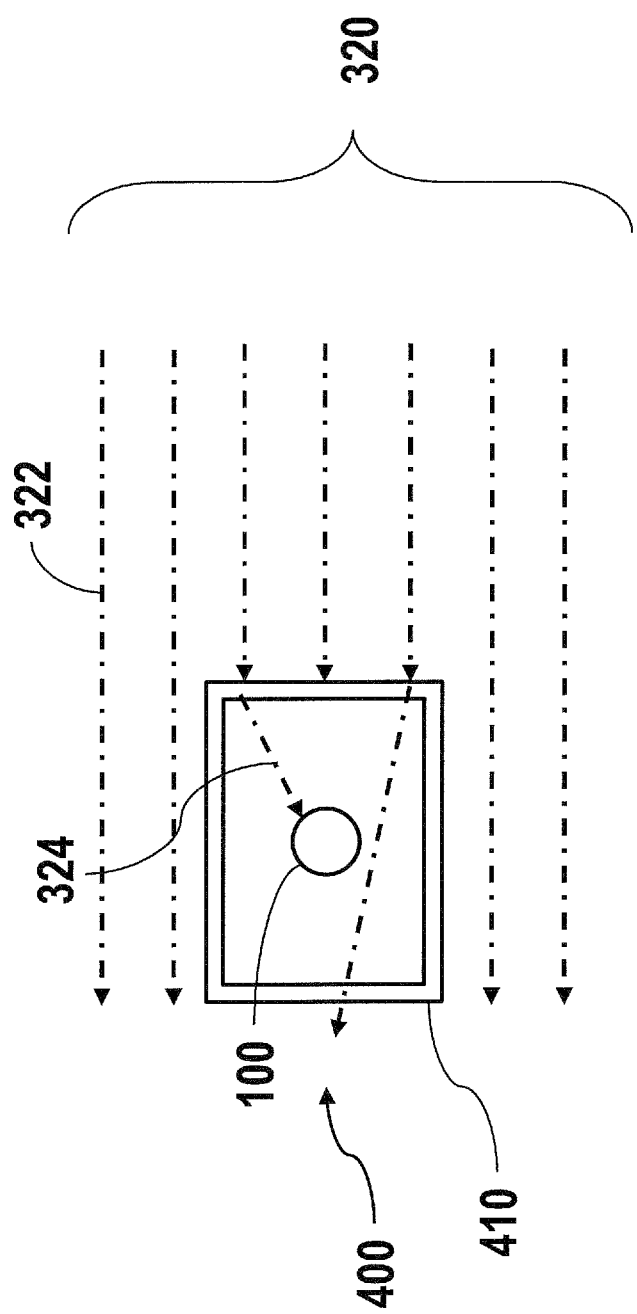
FIG. 5 is a top-view illustration of the moderated neutron sensor of FIG. 4 within a field of neutron flux, in accordance with the first exemplary embodiment of the present disclosure.

FIG. 5 is a top-view illustration of the moderated neutron sensor 400 of FIG. 4 within a field of neutron flux 320, in accordance with the first exemplary embodiment of the present disclosure. The moderated neutron sensor 400 includes the neutron detector 100 and the moderating enclosure 410. Just like in FIG. 3, above, the neutrons 322 in the field of neutron flux 320 propagate in a straight line toward and near the moderated neutron sensor 400. However, unlike in FIG. 3, a greater number of neutrons 322 interact with the moderating enclosure 410 and are directed toward the neutron detector 100. Neutrons 324 that would have otherwise missed the neutron detector 100 may now be read by the moderated neutron sensor 400. It should be noted that not all neutrons 324 that interact with the moderating enclosure 410 will be directed to the neutron detector 100. However, a greater portion of the neutron flux 320 may be directed to the neutron detector 100, resulting in an overall increase in sensitivity.

Figure 6:
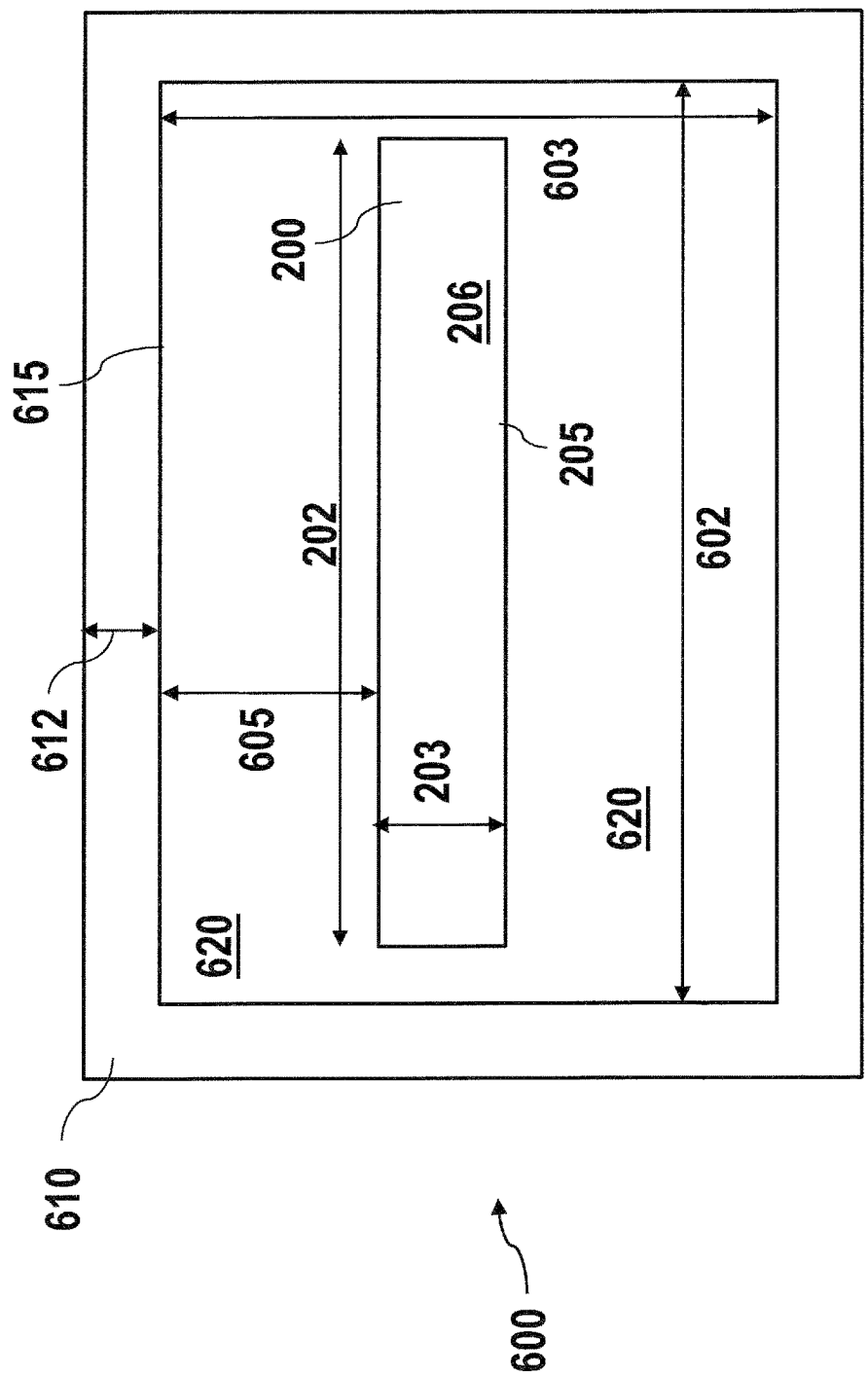
FIG. 6 is a cross-sectional illustration of a sheet form factor moderated neutron sensor, in accordance with the first exemplary embodiment of the present disclosure.

FIG. 6 is a cross-sectional illustration of a sheet form factor moderated neutron sensor ("moderated neutron sensor") 600, in accordance with the first exemplary embodiment of the present disclosure. The sheet form factor moderated neutron sensor 600 is generally similar to the tube form factor moderated neutron sensor 400 of FIG. 4, above. The sheet form factor is shown for purposes of illustration.

The moderated neutron sensor 600 may include a neutron detector 200 having a first volume. A moderating enclosure 610 is positioned around the neutron detector 200 and encloses a second volume. The second volume is between 2 and 80 times larger than the first volume. In one example, the second volume is between 2 and 20 times larger than the first volume. In another example, the second volume is between 5 and 10 times larger than the first volume.

The moderating enclosure 610 may be positioned around the neutron detector 200 and may surround and enclose the entire neutron detector 200. In one example, the thickness 612 of the moderating enclosure 610 may be between about 0.5 inches and 1.5 inches. In another example, the thickness 612 of the moderating enclosure 610 may be greater than 2.0 inches. For example, in applications with higher energy, more monoenergetic neutrons, such as a 5 MeV neutron source, the thickness 612 of the moderating enclosure 610 may be about 2.5 inches. The moderating enclosure 610 may enclose a second volume, which may be determined from the interior width 602, interior depth 603, and interior length of the moderating enclosure (not shown due to perspective). The interior width 602, interior depth 603, and interior length may be the distance between opposing interior surfaces 615 of the moderating enclosure 610.

In one example, the second volume may be larger than the first volume due primarily to a difference between the depth 203 of the neutron detector 200 (shown in FIG. 2A) and the depth 603 of the moderating enclosure 610. Thus, the difference between the depth 203 of the neutron detector 200 and the interior depth 603 of the moderating enclosure 610 may be larger than the difference between the length 101 of the neutron detector 200 and the length of the moderating enclosure 610. In other words, the moderating enclosure 610 may be spaced a greater distance from the neutron detector 200 along the depth direction than along the length direction.

In one example, the neutron detector 200 may be located centrally within the moderating enclosure 610.

In one example, the relationship between the neutron detector 200 and the moderating enclosure 610 may be understood as a function of the distance 605 between an exterior surface 205 of the neutron detector 200 and an interior surface 615 of the moderating enclosure 610 ("spaced distance" 605). A moderated neutron detector 600 includes a neutron detector 200 having an exterior surface 205. A moderating enclosure 610 is positioned around the neutron detector 200. The moderating enclosure 610 has an interior surface 615 positioned a spaced distance 605 away from the exterior surface 205 of the neutron detector 200 by at least one half inch. Thus, for any given thickness 612 of the moderating enclosure 610, the moderating enclosure 610 and the neutron detector 200 may be positioned a spaced distance apart. In one example, the spaced distance 605 may be at least 0.5 inches. In another example, the spaced distance may be at least 2 inches. In another example the spaced distance may be at least 3 inches. When the neutron detector 200 and moderating enclosure 610 have different widths 202, 602 and depths 203, 603, as shown in FIG. 6, the spaced distance 605 may not be constant at every point between the exterior surface 205 of the neutron detector 200 and the interior surface of the moderating enclosure 610. The spaced distance 605 may be considered to be the minimum distance between any two points on the exterior surface 205 and interior surface 615. In this case, the minimum distance between any two points on the exterior surface 205 and the interior surface 615 may be at least 0.5 inches. In another example, the spaced distance 605 may be measured along the length 101 of the neutron detector 200, but not from an end surface 206 of the neutron detector 200. In one example, the spaced distance 605 may not be, measured from the plane of the end surface 206, but may only be considered from the exterior surface 205 in an orthogonal plane.

The interior 620 between the neutron detector 200 and the moderating enclosure 610 may include anything that is substantially transparent to the passage of neutrons, as discussed relative to FIG. 4, above.

Operating Examples

Figure 7:
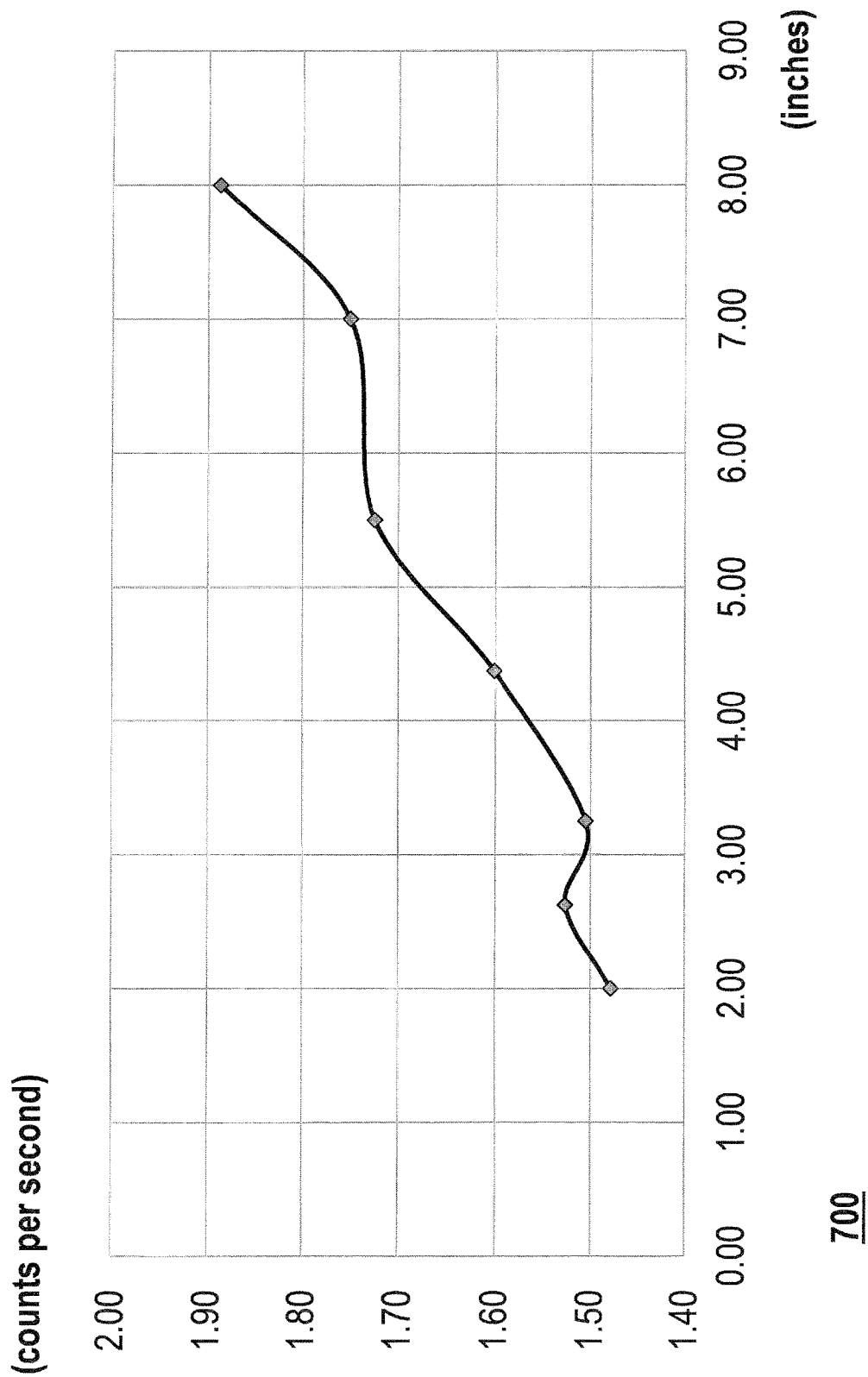
FIG. 7 is an exemplary graph showing neutron sensor sensitivity as a function of moderator depth for a lithium-6 panel detector, in accordance with the first exemplary embodiment of the present disclosure.

FIG. 7 is an exemplary graph 700 showing neutron sensor sensitivity as a function of moderator depth for a lithium-6 panel detector, in accordance with the first exemplary embodiment of the present disclosure. A moderated neutron sensor was constructed according to the disclosure in FIG. 6, above. A Li-6 detector was positioned in a moderating enclosure having about 1 inch thickness. The length and width of the moderating enclosure were fixed during each measurement, but the depth of the moderating enclosure was increased during each measurement. The neutron count was measured for each iteration of the moderating enclosure depth. The depth values used and resultant sensitivity counts are shown in Table 1, below.

TABLE 1

Moderating Enclosure Depth vs. Detector Sensitivity

| Moderating Enclosure Depth (inches) | Sensitivity (counts per second) |
|---|---|
| 8.00 | 1.89 |
| 7.00 | 1.75 |
| 5.50 | 1.72 |
| 4.38 | 1.60 |
| 3.25 | 1.51 |
| 2.63 | 1.53 |
| 2.00 | 1.48 |

The data from the graph 700 in FIG. 7 seems to indicate that, for this type and shape of moderated neutron sensor, a deeper moderating enclosure correlates with an increase in moderated neutron sensor sensitivity. At a depth of 8 inches, the moderated neutron sensor counted about 27% more neutrons per second than the sensor with a moderating enclosure at a depth of 2 inches.

In another operating example, the moderating enclosure described in FIGS. 4 and 6 was built having interior dimensions of 42"×10"×8" (length×width×depth) and a thickness of 1". A number of neutron detectors were sequentially positioned within the moderating enclosure and used to measure neutrons detected per hour. The neutron detectors were 2 inch diameter He3 detectors of 12 inch and 40 inch lengths, 2 inch, 3 inch, and 4 inch BF3 detectors of 33 inch lengths, and a 38 inch Li6 panel. The neutron detectors were also positioned within prior art close-fit moderators and used to measure neutrons detected per hour under similar conditions. In another aspect of this example, multiple detectors were positioned within the moderating enclosure, and measurements were taken. The data is shown in Table 2, below.

TABLE 2

Detector Count vs. Moderator Size

| | Number of Tubes | 2" × 12" He3 | 2" × 33" BF3 | 3" × 33" BF3 | 4" × 33" BF3 | 38" Li Panel | 2" × 40" He3 |
|---|---|---|---|---|---|---|---|
| Close fit moderator (tube) | 1 | 1,378 | 2,055 | 3,352 | | | 5,112 |
| Close fit moderator (sheet) | 1 | | | | 5,235 | 4,932 | |
| Moderating Enclosure | 1 | | 2,868 | 5,297 | 7,058 | 6,468 | 10,132 |
| | 2 | | 5,371 | 8,956 | 10,978 | | |
| | 3 | | 6,935 | 11,001 | | | |
| | 4 | | 8,751 | 12,684 | | | |
| | 5 | | 9,910 | | | | |
| | 6 | | 11,146 | | | | |

Table 2 shows that each neutron detector saw an increased count over the measurement period when a moderating enclosure was added instead of a close fit moderator. The detector count values from Table 2 were then normalized using the detector count values for each neutron detector with a close fit moderator. The normalized results are shown in Table 3, below as detector sensitivity vs. moderator size. The detector count values in Table 3 are expressed as a ratio of the actual count rate to the count rate of the detectors using close fit moderators. The sensitivity for each detector with a close-fit moderator is set to 1, while the sensitivity for each detector with a moderating enclosure is set as a ratio.

TABLE 3

Normalized Detector Sensitivity vs. Moderator Size

| | Number of Tubes | 2" × 12" He3 | 2" × 33" BF3 | 3" × 33" BF3 | 4" × 33" BF3 | 38" Li Panel | 2" × 40" He3 |
|---|---|---|---|---|---|---|---|
| Close fit moderator | | | 1 | 1 | 1 | 1 | 1 |
| Moderating Enclosure | 1 | | 1.4 | 1.58 | 1.35 | 1.31 | 1.98 |
| | 2 | | 2.61 | 2.67 | 2.1 | | |
| | 3 | | 3.37 | 3.28 | | | |
| | 4 | | 4.26 | 3.78 | | | |
| | 5 | | 4.82 | | | | |
| | 6 | | 5.42 | | | | |

The data from Table 3 shows improvement in sensitivity for each of the detectors in a moderating enclosure. For example, the 3" OD×33" BF3 detector goes from 1 to 1.58, a significant sensitivity enhancement. For the 2" OD×40" He3 tube the enhancement is nearly 2. For BF3, the biggest increase going from a close fitted (cylindrical or rectangular) moderator to the moderating enclosure is realized with the 3" OD tube. The size of the moderating enclosure (42×12×10) is just such that it best enhances the 3" OD tube. For any given tube diameter, going from a close fit moderator to larger sizes must create a count rate graph that increases at first but which may eventually decrease. During initial increase of moderating enclosure size, more neutrons are captured, and the additional flux increases the count rate; as the moderator continues to increase, more flux is captured, but the interior volume is large enough that the tube samples an increasingly small fraction of that volume. So, the count increase may actually reach a maximum at some particular size, then decrease with increased size. The count increases of 1.4, 1.58 and 1.35 for the 2", 3" and 4" tubes, respectively, indicate that that 2" tube may already be past its maximum; the 3" tube may be near a maximum; and the 4" tube has not yet achieved a maximum—the moderating enclosure is not large enough. Given the chosen moderating enclosure size, the 3" OD BF3 tube has the best enhancement, with a volume ratio of 20:1 between detector and moderating enclosure. The volume ratios for the 2", 3" and 4" OD detectors are: 40:1, 20:1 and 10:1, respectively.

It is noted that the He3 (2" OD×40") detector has the largest sensitivity enhancement, which is nearly 2. This may be due to the He3 neutron detector itself, which is more sensitive per unit of volume than the other neutron detectors tested. It is worth noting this enhancement. For mobile detectors using He3, larger moderating enclosures may result in a significant sensitivity enhancement, which in turn may result in a much less costly moderated neutron sensor.

Figure 8:
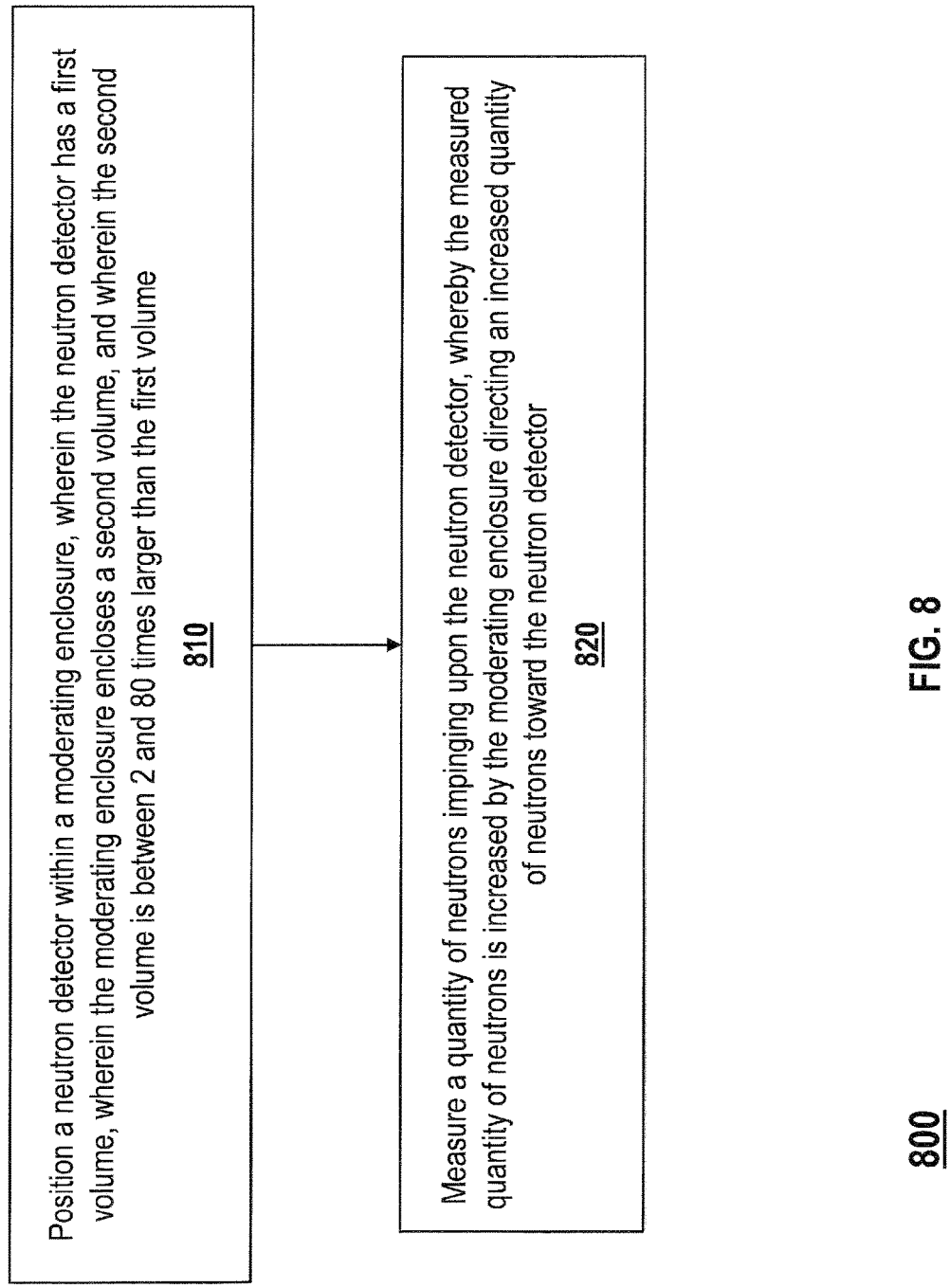
FIG. 8 is a flow chart showing a method for increased neutron detection, in accordance with a second exemplary embodiment of the present disclosure.

FIG. 8 is a flow chart 800 showing a method for increased neutron detection, in accordance with a second exemplary embodiment of the present disclosure. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

Step 810 includes positioning a neutron detector within a moderating enclosure, wherein the neutron detector has a first volume, wherein the moderating enclosure encloses a second volume, and wherein the second volume is between 2 and 80 times larger than the first volume.

The neutron detector ("neutron detector") may be any neutron detector discussed relative to FIGS. 1A-7, above. The volume of the neutron detector may be the volume occupied by the detector and any tube, sheet, or other structure that holds, contains, or supports the active elements within the neutron detector. The moderating enclosure may be any moderating enclosure discussed relative to FIGS. 1A-7, above. The second volume enclosed by the moderating enclosure may be the interior volume determined by the interior length, interior width, and interior depth of the moderating enclosure. In one example, the second volume may be between 2 and 80 times larger than the first volume. In another example, the second volume may be between 2 and 20 times larger than the first volume. In another example, the second volume may be between 5 and 10 times larger than the first volume.

In another example, the second volume may be larger than the first volume due primarily to a difference between the depth of the neutron detector and the depth of the moderating enclosure. Thus, the difference between the depth of the neutron detector and the interior depth of the moderating enclosure may be larger than the difference between the length of the neutron detector and the length of the moderating enclosure. In other words, the moderating enclosure may be spaced a greater distance from the neutron detector along the depth direction than along the length direction.

There may be a spaced distance between an exterior surface of the neutron detector and an interior surface of the moderating enclosure. The spaced distance may create an interior volume. The interior volume may include anything substantially transparent to the passage of neutrons, including a vacuum, gases such as air, liquids, or solid materials.

In one example, the neutron detector may be centrally located within the moderating enclosure.

In one example, the thickness of the moderating enclosure may be between 0.5 and 2.0 inches. In another example, the thickness of the moderating enclosure may be greater than 2.0 inches. For example, in applications with higher energy, more monoenergetic neutrons, such as a 5 MeV neutron source, the thickness of the moderating enclosure may be about 2.5 inches.

Step 820 includes measuring a quantity of neutrons impinging upon the neutron detector, whereby the measured quantity of neutrons is increased by the moderating enclosure directing an increased quantity of neutrons toward the neutron detector.

Depending on the intended use and type of neutron detector, measuring a quantity of neutrons may be implemented in a number of ways. For instance, the moderated neutron sensor, which can be considered the neutron detector, moderating enclosure, and associated components, may be positioned above a measurement surface or proximate to a measurement area. The position of the moderated neutron sensor may be located in the path of a field of neutron flux. Neutrons may impinge upon the neutron detector. The moderated neutron sensor may record the quantity of neutrons impinging upon the detector over a desired period of time. This number may be stored in memory, transmitted via a network, or further processed for analysis.

The moderated neutron sensor may be implemented in a number of forms. For example, the moderated neutron sensor may be part of a portal monitor searching for nuclear material passing through an area. In another example, the moderated neutron sensor may be deployed on a vehicle such as an automobile, airplane, unmanned aerial vehicle, and the like. In another example, the moderated neutron sensor may be deployed on a tower, tall building, or satellite.

The measured quantity of neutrons may be increased by the moderating enclosure directing an increased quantity of neutrons toward the neutron detector. This increase may be relative to a bare neutron detector or a neutron detector having a prior art close fit moderator. In one example, the measured quantity of neutrons may be increased by a factor greater than 1.3. In another example, the measured quantity of neutrons may be increased by a factor greater than 1.5. In a particular example, the measured quantity of neutrons may be increased by a factor greater than 1.9.

The method may further include any other features, components, or functions disclosed relative to any other figure of this disclosure.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A moderated neutron sensor, comprising:
a single, cylindrically-shaped neutron detector having a diameter dimension, $D_1$; and
a moderating enclosure positioned around the single, cylindrically-shaped neutron detector and enclosing the single, cylindrically-shaped neutron detector therein, the moderating enclosure having a width dimension, $D_2$, measured between opposing interior sidewalls having a closest distance therebetween of all sidewalls of the moderating enclosure, wherein a sensitivity of the single, cylindrically-shaped neutron detector is a function of a ratio between $D_1$ and $D_2$, wherein $D_2$ is equal to or greater than $D_1$ plus substantially 1.0 inch.

2. The moderated neutron sensor of claim 1, wherein the single, cylindrically-shaped neutron detector is centrally located within the moderating enclosure.

3. The moderated neutron sensor of claim 1, wherein a thickness of the moderating enclosure is between 0.5 and 2.0 inches.

4. The moderated neutron sensor of claim 1, wherein the single, cylindrically-shaped neutron detector further comprises a Helium-3 (He3) detector.

5. A moderated neutron sensor, comprising:
a single, non-cylindrically-shaped neutron detector having an elongated axial length, a first width dimension, $D_1$, and a second width dimension, $D_2$, wherein $D_1$ and $D_2$ are measured perpendicular to the elongated axial length; and
a non-cylindrically-shaped moderating enclosure positioned around the single, non-cylindrically-shaped neutron detector, the non-cylindrically-shaped moderating enclosure has a third width dimension, $D_3$, as measured between opposing interior sidewalls of the moderating enclosure, and a fourth width dimension, $D_4$, as measured between opposing interior sidewalls of the moderating enclosure, wherein $D_3$ and $D_4$ are axially aligned with $D_1$ and $D_2$, respectively, wherein a sensitivity of the single, non-cylindrically-shaped neutron detector is a function of a ratio between at least one of: $D_1$ and $D_3$ or $D_2$ and $D_4$, wherein $D_3$ is equal to or greater than $D_1$ plus substantially 1.0 inch and $D_4$ is equal to or greater than $D_2$ plus substantially 1.0 inch.

6. The moderated neutron sensor of claim 5, wherein the single, non-cylindrically-shaped neutron detector is centrally located within the non-cylindrically-shaped moderating enclosure.

7. The moderated neutron sensor of claim 5, wherein a thickness of the non-cylindrically-shaped moderating enclosure is between 0.5 and 2.0 inches.

8. The moderated neutron sensor of claim 5, wherein the single, non-cylindrically-shaped neutron detector further comprises a Helium-3 (He3) detector.

9. A method for increased sensitivity of neutron detection, comprising the steps of:
positioning a single neutron detector within a moderating enclosure, whereby a minimum spaced distance is formed between an exterior surface of the single neutron detector and an interior surface of the moderating enclosure at a closest distance therebetween, wherein a difference between a depth of the single neutron detector and a depth of the moderating enclosure is larger than a difference between a length of the single neutron detector and a length of the moderating enclosure; and
detecting a quantity of neutrons with the single neutron detector, wherein a sensitivity level of the single neutron detector correlates with a radial volume formed within the minimum spaced distance between the exterior surface of the single neutron detector and the interior surface of the moderating enclosure.

10. The method of claim 9, wherein the single neutron detector is centrally located within the moderating enclosure.

11. The method of claim 9, wherein the radial volume is between 2 and 20 times larger than a volume of the single neutron detector.

12. The method of claim 9, wherein the radial volume is between 5 and 10 times larger than a volume of the single neutron detector.

13. The method of claim 9, wherein a thickness of the moderating enclosure is between 0.5 and 2.0 inches.

14. The method of claim 9, wherein the sensitivity level of the single neutron detector is increased over a neutron detector having a close fit moderator by a factor greater than 1.3.

15. The method of claim 9, wherein the sensitivity level of the single neutron detector is increased over a neutron detector having a close fit moderator by a factor greater than 1.5.

16. The method of claim 9, wherein the single neutron detector further comprises a Helium-3 (He3) detector.

* * * * *